(12) United States Patent
Kim et al.

(10) Patent No.: US 8,093,561 B2
(45) Date of Patent: Jan. 10, 2012

(54) THYROID UPTAKE MEASUREMENT APPARATUS

(75) Inventors: Yong Kown Kim, Nonsan-si (KR); Jin hun Joung, Cheongju-si (KR); Seung Jae Lee, Wonju-si (KR)

(73) Assignee: NuCare Medical Systems, Inc. (KR)

( * ) Notice: Subject to any disclaimer, the term of this patent is extended or adjusted under 35 U.S.C. 154(b) by 0 days.

(21) Appl. No.: 12/681,324

(22) PCT Filed: Nov. 24, 2009

(86) PCT No.: PCT/KR2009/006908
§ 371 (c)(1),
(2), (4) Date: Apr. 1, 2010

(87) PCT Pub. No.: WO2011/043511
PCT Pub. Date: Apr. 14, 2011

(65) Prior Publication Data
US 2011/0213246 A1      Sep. 1, 2011

(30) Foreign Application Priority Data

Oct. 9, 2009    (KR) .................. 10-2009-0096057

(51) Int. Cl.
*G01T 1/20*    (2006.01)

(52) U.S. Cl. ............................... 250/361 R; 250/370.07
(58) Field of Classification Search ............. 250/361 R, 250/362, 370.07
See application file for complete search history.

(56) References Cited

U.S. PATENT DOCUMENTS

| 6,814,489 B2 | 11/2004 | Jensen et al. |
| 2004/0015320 A1 | 1/2004 | Nagaoka et al. |

FOREIGN PATENT DOCUMENTS

| CN | 1585621 A | 2/2005 |
| EP | 1346667 A1 | 9/2003 |
| JP | 2002168957 A | 6/2002 |
| JP | 2003265543 A | 9/2003 |
| KR | 20010060301 A | 7/2001 |
| KR | 20020023394 A | 3/2002 |
| KR | 2003-0076348 A | 9/2003 |
| KR | 10-2005-0090667 A | 3/2004 |
| KR | 10-2005-0009235 Y1 | 5/2005 |
| KR | 10-0962787 B1 | 6/2010 |
| WO | WO 03/045242 A1 | 6/2003 |

OTHER PUBLICATIONS

Wai-Hoi Wong et al., "A Scintillation Detector Signal . . . ", paper, 1998, 5 pages, pp. 145-149, IEEE, University of Texas MD Anderson Cancer Center.
Feyzi Inanc, "Analysis of X-Ray and Gamma Ray Scattering . . . ", paper, known prior to Apr. 1, 2010, 17 pages, Iowa State University Center for Nondestructive Evaluation.

*Primary Examiner* — Mark R Gaworecki
(74) *Attorney, Agent, or Firm* — Levenfeld Pearlstein, LLC

(57) ABSTRACT

Disclosed is a thyroid uptake measurement apparatus, in which a radiation attenuation filter is detachably provided at the leading end of a collimator of a radiation detector. The radiation attenuation filter inhibits the saturation of signals when gamma rays exceeding the maximum counting rate are entered. Accordingly, it is possible to inhibit the distortion of signals when the pile-up of the signals increases by an increase in the radiation decay. Moreover, the use of the radiation attenuation filter can significantly improve the scatter fraction, that is, the ratio of scattered radiation/total radiation generated by material scatter of radiation.

4 Claims, 1 Drawing Sheet

THYROID UPTAKE MEASUREMENT APPARATUS

CROSS-REFERENCE TO RELATED APPLICATIONS

This patent application is the National Stage of International Application No. PCT/KR2009/006908, filed Nov 24, 2009, that claims the benefit of Korean Application No. 10-2009-0096057, filed Oct 9, 2009, the entire teachings and disclosure of which are incorporated herein by reference thereto.

BACKGROUND OF THE INVENTION

1. Field of the Invention

The present invention relates to a thyroid radiation uptake measurement apparatus, and more particularly to a thyroid radiation uptake measurement apparatus for measuring an uptake extent of a radioisotope adsorbed in a thyroid to determine if the thyroid is functionally abnormal.

2. Description of the Prior Art

As generally known in the art, a thyroid is an endocrine organ secreting a thyroid hormone controlling a body's metabolism, which is positioned in front of a thyroid cartilage. Thyroid diseases include thyrotoxicosis, hypothyroidism, thyroiditis, thyroid nodule, thyroid cancer, and the like.

From among various apparatuses used for diagnosing a thyroid disease, a thyroid uptake measurement apparatus is especially an apparatus using nuclear medicine, in which the adsorption/uptake extent of an orally administered (or intravenously injected) radioisotope, such as, iodine ($^{123}$I or $^{131}$I) or $^{99\mu}$Tc (Technetium), on a thyroid is measured to determine if the thyroid is abnormal.

A radiation detector which is a main component of a conventional thyroid uptake measurement apparatus generally includes a photomultiplier, a scintillator, and a collimator.

In the operation process of the above mentioned conventional thyroid uptake measurement apparatus, when gamma rays emitted from radiation adsorbed in a thyroid react to the scintillator via the collimator, the incident gamma rays are converted into light, and the light is converted into electrical signals via the photomultiplier. Herein, a high voltage of up to several thousand volts (V) is applied so that the photomultiplier can carry out amplification through conversion of the light into electrons. For this reason, a separate high-voltage generating device is required. Also, the electrical signals generated from the photomultiplier are amplified via an amplifier circuit, and the amplified signals are processed to be used for obtaining quantitative information of radiation.

A protocol for such a thyroid test is differently carried out depending on the kind of radiation used and the object of test. However, a basic procedure is based on the method suggested by Society of Nuclear Medicine (SNM). The kinds of radioisotopes used and the levels of injected drugs are noted in "Radiation dosimetry for adults" in Table 1.

TABLE 1

| Radiopharma-ceutical | Administered activity MBq(mCi) | Organ receiving the largest radiation dose mGy/MBq(rad/mCi) | Effective dose equivalent mSv/MBq(rem/mCi) |
| --- | --- | --- | --- |
| NaI-123 iodide* | 3.7-11.1po (0.1-0.3) | 3.2 Thyroid(12.0) | 0.11 (0.41) |
| $^{99m}$Tc-pertechnetate (TcO$_4^-$) | 74-370 (2-10) | 0.062 ULI** (0.23) | 0.013 (0.048) |
| NaI-31I iodide | 0.15-0.37po (0.004-0.01) | 360 Thyroid (1300) | 11 (41.0) |

*assuming 25% uptake
**ULI—upper large intestine
References:
1. Micheal F. Stabin, PhD, CHP: Radiation Internal Dose Information Center, Oak Ridge Institute for Sience and Education, Oak Ridge, TN, 1996.
2. ICRP Publication 53, Radiation Dose to Patients from Radiopharmaceuticals, 1994 edition.
3. Loevinger R, Budinger T, Watson, E: MIRD Primer for Absorbed Dose Calculations, Society of Nuclear Medicine, 1991.

Meanwhile, in a general process of the thyroid uptake measurement, the distance from a scintillator of a detector to a thyroid is maintained within a range of about 25 to 30 cm. In a case where an isotope of iodine is used, the measurement is generally carried out after about 18~24 hours from the administration of the radiopharmaceutical. Additionally, the measurements may be carried out after 2 hours and 6 hours from the administration.

Herein, a neck, thigh (for background measurement), and a neck phantom (before and after administration of dose) are measured. An RAIU (Radioiodine uptake) is calculated using the equation below.

$$RAIU = \frac{Neckcounts(cpm) - ThighCounts(cpm)}{Ad \text{ min} \cdot Counts(cpm) - BackgroundCounts(cpm)} \times 100 \, [\%] \quad (1)$$

In a case where Tc99m Pertechnetate (TcO$_4^-$) is used, it is easy to secure a radioisotope, and it is possible to carry out uptake measurement after about 10~20 minutes from an intravenous injection. Thus, compared to a conventional iodine ($^{123}$I or $^{131}$I) methods, it has following advantages; 1) the radiation exposure of the body can be significantly reduced, 2) the convenience of a patient and a technician is improved, 3) a cost is reduced, and 4) in a case where $^{99m}$Tc imaging study (image acquisition using $^{99m}$Tc) is simultaneously carried out to obtain a thyroid image, the convenience is increased.

By the recent general use of $^{99m}$Tc Pertechnetate (TcO$_4^-$) thyroid imaging with a gamma camera, a thyroid uptake measurement using $^{99m}$Tc Pertechnetate (TcO$_4^-$) shows a tendency to be carried out prior to thyroid imaging.

However, when an isotope of 5~10 mCi is administered to acquire an image, a conventional thyroid uptake measurement apparatus is easily saturated due to its low counting capacity. Thus, a thyroid uptake measurement is generally carried out prior to an image test by injecting a small amount (about 0.5 mCi) of isotope.

Therefore, inconvenience will not be avoidable in that an intravenous injection has to be delivered to a patient twice, i.e., one for thyroid uptake and the other for thyroid imaging. Also, there is a problem in that from the standpoint of a patient management, the throughput is ineffective.

Also, even if a high counting-rate thyroid uptake measurement apparatus exists, the reliability on the measured data collected for thyroid radiation uptake calculation is significantly reduced due to pile-up of radiation signal in consideration of the geometrical structure of a thyroid measurement apparatus and the radiation generation per unit time of 5~10 mCi of isotope.

SUMMARY OF THE INVENTION

Accordingly, the present invention has been made to solve the above-mentioned problems occurring in the prior art, and the present invention provides a thyroid radiation uptake measurement apparatus, in which by only one administration (5 to 10 mCi) of $^{99m}$Tc Pertechnetate, a thyroid image of a gamma camera is obtained while the thyroid radiation uptake measurement is carried out without lowering the reliability of the test.

In accordance with an aspect of the present invention, there is provided a thyroid radiation uptake measurement apparatus for measuring an uptake extent of a radioisotope in a thyroid by using a radiation detector to determine if the thyroid is abnormal, wherein the radiation detector includes: a collimator which takes a pipe shape in such a manner that gamma rays emitted from the radioisotope taken in the thyroid are entered into the collimator; a scintillator provided within the collimator, which converts the gamma rays entered into the collimator into light according to its energy; a photomultiplier fitted in a trailing end portion of the collimator on the scintillator, and converts the light converted by the scintillator into electrical signals according to a light quantity; and a radiation attenuation filter is detachably provided at a leading end portion of the collimator, and attenuates an amount of the gamma rays entered into the collimator.

Herein, the radiation attenuation filter includes at least one layered metallic filter plate, and the thickness of the metallic filter plate is calculated by $e^{-\mu t}$=transmitted radiation % according to a predetermined transmission amount of the gamma rays (herein, t denotes the thickness of the metallic filter plate, and μ denotes an attenuation coefficient of a material used for the metallic filter plate).

Also, preferably, the radiation attenuation filter further includes a reinforcing plate on at least one side end portion thereof in a layering direction of the metallic filter plate.

In the thyroid radiation uptake measurement apparatus according to the present invention, the radiation attenuation filter is detachably provided at the leading end of the collimator of the radiation detector. Accordingly, in the radiation uptake measurement, the amount of the gamma rays entering into the collimator is properly adjusted by the radiation attenuation filter. This inhibits the pile-up of the gamma rays and the saturation of converted signals due to the radiation detector's excess of the maximum counting rate. Thus, by only one injection (5 to 10 mCi) of high $^{99m}$Tc Pertechnetate dose, it is possible to not only obtain a thyroid image with a gamma camera, but also to carry out the thyroid radiation uptake measurement without lowering the reliability of the test.

Also, in the thyroid radiation uptake measurement apparatus according to the present invention, the radiation attenuation filter is used to reduce noise (scatter) of the radiation source. This increases a signal-to-noise ratio of the incident radiation, thereby improving the reliability of the test.

Also, in the thyroid radiation uptake measurement apparatus according to the present invention, the radiation attenuation filter includes a plurality of different metallic filter plates which are layered upon each other, or further includes a reinforcing plate in addition to the metallic filter plate, so as to reinforce the mechanical strength of the radiation attenuation filter.

BRIEF DESCRIPTION OF THE DRAWINGS

The above and other objects, features and advantages of the present invention will be more apparent from the following detailed description taken in conjunction with the accompanying drawings, in which.

DETAILED DESCRIPTION OF THE EXEMPLARY EMBODIMENTS

Figure 1:
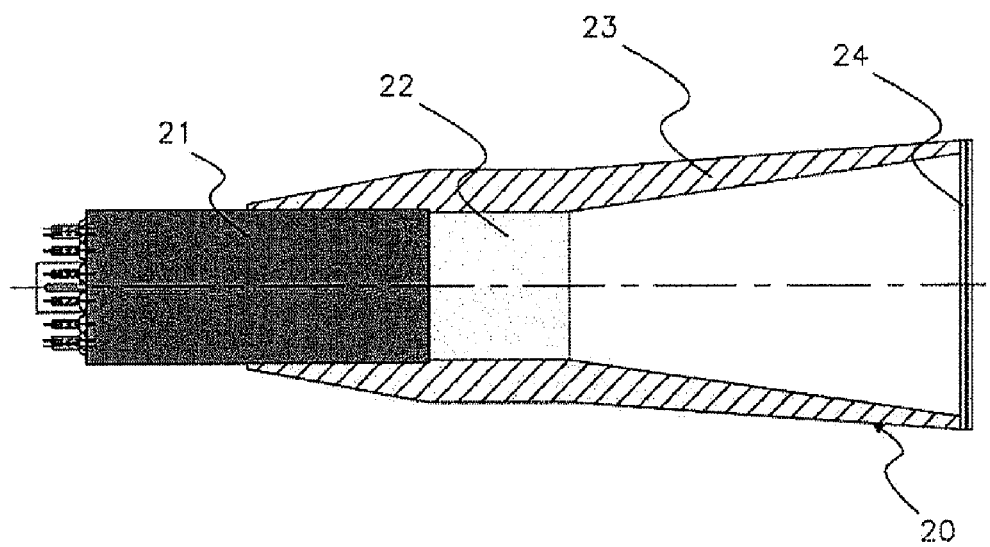
FIG. 1 is a schematic view illustrating a radiation detector of a thyroid radiation uptake measurement apparatus according to an embodiment of the present invention.

Hereinafter, an exemplary embodiment of the present invention will be described in detail with reference to the accompanying drawing so that a person skilled in the art can readily carry out the invention. However, the present invention may be embodied in various forms without being limited to the embodiment described hereinafter. In order to clarify the present invention, some parts unrelated to the description are omitted from the drawing. In the following description, the same reference numerals are used to designate the same or similar components.

FIG. 1 is a schematic view illustrating a radiation detector of a thyroid radiation uptake measurement apparatus according to an embodiment of the present invention.

Referring to FIG. 1, the thyroid radiation uptake measurement apparatus according to the present embodiment is configured in such a manner that a radiation detector 20 is used to measure the adsorption/uptake extent of an orally administered (or intravenously injected) radioisotope, that is, $^{9m}$Tc Pertechnetate (5-10 mCi), on a thyroid to determine if the thyroid is abnormal.

In the present embodiment, the radiation detector 20 includes a collimator 23, a scintillator 22, a photomultiplier 21, and a radiation attenuation filter 24.

The collimator 23 takes a pipe shape in such a manner that gamma rays emitted from the radioisotope adsorbed (or taken) in the thyroid are entered to the inside through the leading end portion.

In the present embodiment, the collimator 23 has a longitudinal gamma ray incident passage passing through the inside thereof. The gamma ray incident passage takes a diffuser shape (that is, a funnel shape) whose cross-section gradually becomes narrower from the leading end to the trailing end.

The scintillator 22 is provided within the gamma ray incident passage of the collimator 23, and converts the gamma rays entered into the collimator 23 into light according to its energy.

The photomultiplier 21 is fixedly fitted in the trailing end portion of the collimator 23 with respect to the scintillator 22, and converts the light converted by the scintillator 22 into different electrical signals according to the light quantity.

Herein, since the photomultiplier 21 can carry out amplification through the conversion of the light into electrons, a high voltage of up to several thousand volts (V) is applied. For this reason, a separate high-voltage generating device is required.

The electrical signal generated from the photomultiplier 21 is amplified via an amplifier circuit, and the amplified electrical signals are used for obtaining quantitative information of gamma rays.

Also, the radiation attenuation filter 24 is detachably provided at the leading end of the collimator 23, and attenuates the amount of the gamma rays entered into the collimator 23 according to the predetermined thickness of the radiation attenuation filter at a fixed rate.

Herein, the material and the thickness of the metallic filter plate constituting the above mentioned radiation attenuation filter 24 are appropriately selected according to the attenuation extent of the gamma rays entered into the collimator 23, and the requirement. The thickness may be calculated using the equation below.

$$e^{-\mu t} = \text{transmitted radiation \%} \quad (2)$$

Herein, t denotes the thickness of the metallic filter plate, and $\mu$ denotes the attenuation coefficient of the material of the metallic filter plate.

The above mentioned metallic filter plate may include any one material selected from the group including aluminum (AL), lead (Pb), tungsten (W), and an alloy thereof.

Especially, more preferably, the metallic filter plate may include a metallic material with a high atomic number, such as lead (Pb), or tungsten (W). For example, in a case where a radioisotope of 140 keV $^{9m}$Tc is used, the attenuation constants of lead (Pb), and tungsten (W) are 4.15 mm$^{-1}$ and 2.71 mm$^{-1}$, respectively.

For example, when the radiation attenuation filter 24 is designed in such a manner that only 20% of $^{9m}$Tc (140 keV) gamma rays entering into the collimator 23 of the radiation detector 20 can be transmitted, $e^{-\mu t}=0.2$ is obtained from the equation (2). Thus, in this case, when a lead (Pb) metallic filter plate having a thickness of 0.6 mm is used, only 20% of the total amount of the entering gamma rays can be transmitted.

However, although in the above description, the attenuation filter 24 of the present invention includes only a single metallic filter plate, the present invention is not limited thereto. The radiation attenuation filter 24 may include a layered structure having two or more metallic filter plates.

In actuality, the lead (Pb) metallic filter plate having a thickness of 0.6 mm is not solid from the standpoint of the structure. Thus, it is preferable to layer metallic filter plates including aluminum or other metals like a sandwich.

For example, when the radiation attenuation filter 24 is fabricated with a thickness of 2 mm (Al)+0.55 mm (Pb)+2 mm (Al) by using a lead (Pb) metallic filter plate and two aluminum (Al) metallic filter plates, it is possible to achieve the same gamma ray attenuation effect as the above mentioned metallic filter plate including only lead (Pb).

As described above, in the design of the radiation attenuation filter 24, it is very important to correctly select the transmission amount. This is because the use of the radiation attenuation filter 24 with excessive radiation attenuation reduces the sensitivity of the radiation detector, and on the other hand, the use of the radiation attenuation filter 24 with weak radiation attenuation causes the amount of incident gamma rays to exceed the maximum counting rate of the radiation detector 20. In the latter case, the converted electrical signals are saturated, which causes inaccuracy in the measured results.

Also, when a large amount of the radiation source is decayed, a pile-up of gamma rays occurs in the scintillator 22. Thus, it is important to select an appropriate transmission amount which does not cause the pile-up in consideration of an attenuation time constant of the scintillator 22.

In the present exemplary embodiment, as the scintillator 22 for the detection of gamma rays, a NaI(Tl) scintillator is used, and the decay time constant of the NaI(Tl) scintillator is about 250 nsec.

Accordingly, in general, in order to collect 95% or more of the signals of the scintillator 22, a collecting time of 3~4 times as long as the decay time constant is required. If the probabilities are excluded, a collecting time of about 0.75-1 usec is required to avoid pile-ups.

However, the time that any two gamma rays reach the scintillator 22 corresponds to a random event. Statistically, the average required time (an interactive counting rate) in which the probability of pile-up is less than 10% corresponds to a time about 10 times as long as the collecting time.

Accordingly, the detected radiation amount of the radiation detector 20 with respect to an ideal time may be calculated using the equation below.

$$\frac{1}{10X(3X\tau_s)} <= OptimumCountRate <= \frac{1}{10X(4X\tau_s)} \quad (3)$$

Herein, $\tau_s$ denotes a decay constant of the scintillator 22 used for the radiation detector 20.

In the present exemplary embodiment using the NaI(Tl) scintillator 22, in order to avoid the pile-up, it is very important to design the radiation attenuation filter 24 in such a manner that the intensity of the radiation source entering into the collimator 23 of the radiation detector 20 is maintained within a range of 100 to 140 kcps.

Table 2 shows the scatter fraction according to the kind of the radiation attenuation filter.

TABLE 2

|  | Total | True | Scatter | SF % = scatter/ total × 100 |
|---|---|---|---|---|
| Al filter | 16481 | 9250 | 7231 | 44 |
| Pb filter | 8463 | 6419 | 2044 | 24 |
| Al—Pb—Al filter | 8523 | 6483 | 2040 | 24 |
| no filter | 53995 | 31401 | 22594 | 42 |

As noted in Table 2, through a Monte Carlo simulation, it can be found that the use of the radiation attenuation filter 24 improves the scatter fraction (the ratio of scattered radiation/total radiation).

Herein, a radiation source of 18.5 MBq (140 keV) was simulated. In transmitting only about 20% of radiation, when an aluminum (Al) metallic filter plate was used, the thickness of the radiation attenuation filter 24 was 42 mm, and when a lead (Pb) metallic filter plate was used, the thickness of the radiation attenuation filter 24 was 0.6 mm. Also, when the lead (Pb) metallic filter plate and the aluminum (Al) metallic filter plate were layered upon each other, the thickness of the radiation attenuation filter 24 was 2 mm+0.55 mm+2 mm.

As described above, in a case of the radiation attenuation filter 24 including only aluminum (Al), the scatter fraction (SF) was similar to the case where the radiation attenuation filter 24 was not used. This is because aluminum (Al) has a low radiation stopping power in its characteristic, compared to lead (Pb). Thus, the thickness of the radiation attenuation filter 24 was significantly increased up to 42 mm. In this case, as the thickness of the attenuating material increases, the scatter fraction (SF) is linearly increased.

Accordingly, as the material used for the metallic filter plate constituting the radiation attenuation filter 24, a metallic material with a high atomic number, such as lead (Pb), or tungsten (W), is more useful because it can effectively achieve the radiation attenuation with a relatively thin thickness.

Also, beside the above described effects, the radiation attenuation filter 24 can significantly remove noise (scatter) of the radiation source. This increases a signal-to-noise ratio of the incident radiation, thereby improving the reliability of the test.

Meanwhile, the above mentioned radiation attenuation filter 24 may further include a reinforcing plate layered on at least one side thereof in the layering direction of the above mentioned metallic filter plate.

In other words, in the present exemplary embodiment, the lead (Pb) metallic filter plate is very soft, and thus is mechanically not solid and is subject to a change. In this case, in order to reinforce the mechanical strength, the radiation attenuation filter 24 was fabricated, in a sandwich shape, by layering aluminum metallic filter plates and leaving a lead (Pb) metallic filter plate between the plates.

However, as required, the radiation attenuation filter 24 may further include a reinforcing plate for reinforcing the mechanical strength, in addition to the above mentioned aluminum metallic filter.

Herein, like the above described aluminum metallic filter, the reinforcing plate is preferably made of one material selected from the group including woods and plastics, and is layered on at least both sides of the metallic filter plate so as to improve the mechanical strength.

Also, the radiation attenuation filter 24 may be detachably provided at the leading end of the collimator 23 through a structural design, a magnet, or a plastic cover of a unit embedded with metallic filter plates.

Accordingly, in the thyroid uptake measurement, the radiation attenuation filter 24 can be attached or detached to/from the leading end of the collimator 23 as required.

As described above, in the thyroid radiation uptake measurement apparatus according to the present exemplary embodiment, the radiation attenuation filter 24 is detachably provided at the leading end of the collimator 23 of the radiation detector 20. Accordingly, in the radiation uptake measurement, the radiation of the gamma rays entering into the collimator 23 is adjusted via the radiation attenuation filter 24. This inhibits the pile-up of the gamma rays and the saturation of converted signals due to the radiation detector 20's excess of the maximum counting rate. Thus, by only one injection (5 to 10 mCi) of $^{99m}$Tc Pertechnetate, it is possible to not only obtain a thyroid image of a gamma camera, but also to carry out the thyroid radiation uptake measurement without lowering the reliability of the test.

Although an exemplary embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A thyroid radiation uptake measurement apparatus for measuring an uptake extent of a radioisotope in a thyroid by using a radiation detector to determine if the thyroid is abnormal, wherein the radiation detector comprises:
    a collimator which takes a pipe shape in such a manner that gamma rays emitted from the radioisotope taken in the thyroid are entered into the collimator;
    a scintillator provided within the collimator, which converts the gamma rays entered into the collimator into light according to an energy;
    a photomultiplier fitted in a trailing end portion of the collimator on the scintillator, and converts the light converted by the scintillator into electrical signals according to a light quantity; and
    a dose attenuation filter which is detachably provided at a leading end portion of the collimator, and attenuates an amount of the gamma rays entered into the collimator;
    wherein the dose attenuation filter comprises at least one metallic filter plate layered in a transmission direction of the gamma rays, and a thickness of the metallic filter plate is calculated by $e^{-\mu\tau}$=transmission amount % according to a predetermined transmission amount of the gamma rays (herein, t denotes the thickness of the metallic filter plate, and $\mu$ denotes an attenuation constant of a material used for the metallic filter plate).

2. The thyroid radiation update measurement apparatus as claimed in claim 1, wherein the dose attenuation filter further comprises a reinforcing plate on at least one side end portion thereof in a layering direction of the metallic filter plate.

3. The thyroid radiation update measurement apparatus as claimed in claim 2, wherein the metallic filter plate comprises any one material selected from the group including aluminum, lead, tungsten, and an alloy thereof.

4. The thyroid radiation update measurement apparatus as claimed in claim 2, wherein the reinforcing plate comprises any one material selected from the group including woods and plastics.

* * * * *

UNITED STATES PATENT AND TRADEMARK OFFICE
CERTIFICATE OF CORRECTION

| | |
|---|---|
| PATENT NO. | : 8,093,561 B2 |
| APPLICATION NO. | : 12/681324 |
| DATED | : January 10, 2012 |
| INVENTOR(S) | : Yong Kown Kim, Jinhun Joung and Seung Jae Lee |

Page 1 of 1

It is certified that error appears in the above-identified patent and that said Letters Patent is hereby corrected as shown below:

Col. 8, line 37, in claim 3, the phrase "radiation update measurement" should read wherein "radiation uptake measurement".

Col. 8, line 41, in claim 4, the phrase "radiation update measurement" should read wherein "radiation uptake measurement".

Signed and Sealed this
Nineteenth Day of June, 2012

David J. Kappos
*Director of the United States Patent and Trademark Office*